(12) United States Patent
Zamoyski

(10) Patent No.: US 6,346,251 B1
(45) Date of Patent: Feb. 12, 2002

(54) COMPOSITIONS AND METHODS FOR TREATING PSORIASIS

(76) Inventor: Mark Zamoyski, 988 Foothill Dr., San Jose, CA (US) 95123

(*) Notice: Subject to any disclaimer, the term of this patent is extended or adjusted under 35 U.S.C. 154(b) by 0 days.

(21) Appl. No.: 09/965,483

(22) Filed: Sep. 26, 2001

Related U.S. Application Data

(63) Continuation-in-part of application No. 09/459,394, filed on Nov. 24, 1999, which is a continuation-in-part of application No. 09/333,832, filed on Jun. 15, 1999, now abandoned.

(51) Int. Cl.[7] .......................... A61K 35/78; A61K 7/00
(52) U.S. Cl. .............. 424/195.15; 424/401; 424/195.16
(58) Field of Search ............................ 424/195.15, 401

(56) References Cited

U.S. PATENT DOCUMENTS

| | | |
|---|---|---|
| 4,744,981 A | 5/1988 | Pavanasasivam |
| 4,906,452 A | 3/1990 | Sivam |

OTHER PUBLICATIONS

Okazaki et. al., Agricultural and Biological Chemistry, (1989) vol. 53 pp. 1441–1443.
Okazaki et. al., Agricultural and Biological Chemistry, (1988) vol. 52 pp. 795–801.
Dearborn et al, Morbidity and Mortality Weekly Report, Dec. 9, 1994 / vol. 43/No. 48 pp. 881–883.
Usamrild, "Understanding the Threat" Website Printout on Aug. 27, 1999, pp. 2–3 For Human LD50 of T–2.
Magnuson et al, Canadian Journal of Physiology and Pharmacology (1987) vol. 65, No. 5 p. 799 for LD50 of T–2 in Rats.
Lui et al, e Medicine Journal, Aug. 14, 2001 vol. 2, No. 8, 14 pages; p. 5 Summary of Prior Art of Relevance.
Alberts et al, Molecular Biology of the cell, Third Edition pp. 896–897 Re: Disassembling the Cell Cycle Control System.

*Primary Examiner*—Leon B. Lankford, Jr.
*Assistant Examiner*—Susan D. Coe

(57) ABSTRACT

Sesquiterpene epoxide compounds (trichothecenes) and methods for administering such compounds to inhibit proliferation of psoriatic cell populations in the epidermis are disclosed.

4 Claims, 4 Drawing Sheets

COMPOSITIONS AND METHODS FOR TREATING PSORIASIS

Figure 3:
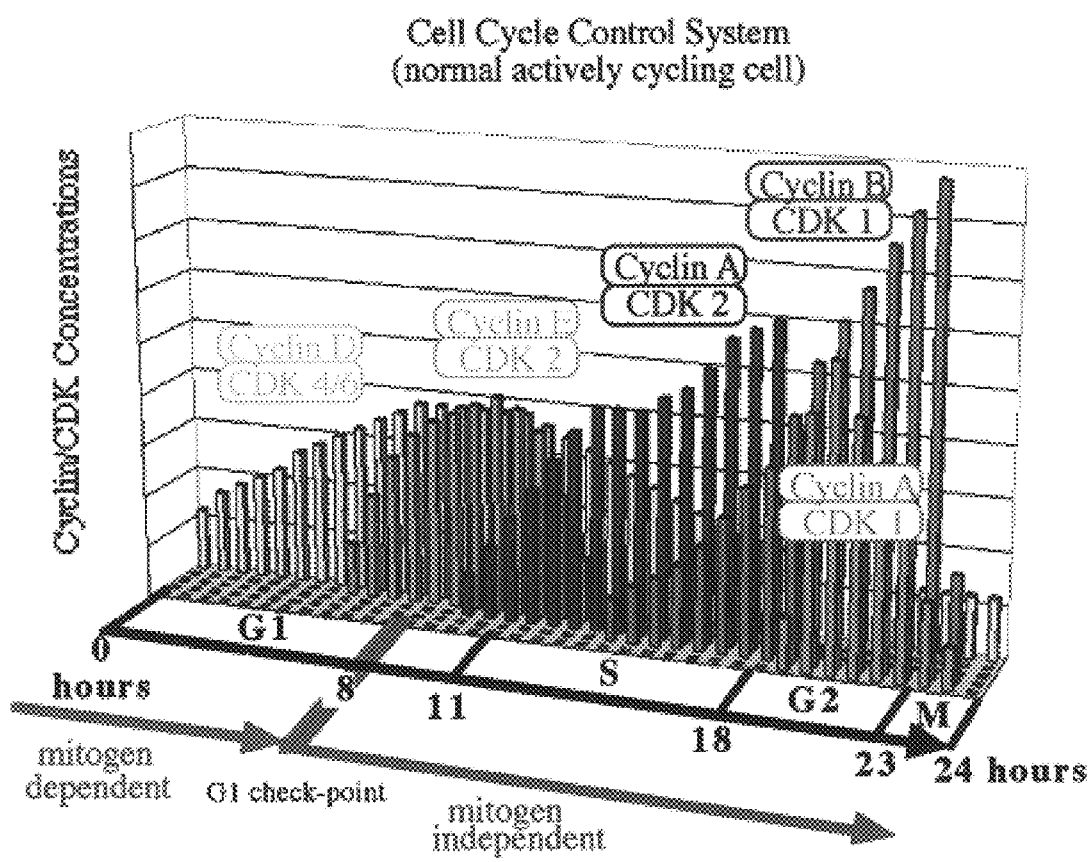

This application is a continuation-in-part of U.S. patent application Ser. No. 09/459,394, filed Nov. 24, 1999, which is a continuation-in-part of U.S. patent application Ser. No. 09/333,832, filed Jun. 15, 1999, now abandoned.

BACKGROUND—SUMMARY

The current invention proposes topical administration of therapeutically effective doses of certain sesquiterpene epoxides (trichothecenes), to inhibit virtually every pathway involved in causing psoriasis.

BACKGROUND

The most fundamental function a cell is protein synthesis (i.e. expression of its DNA). Proteins make up ~60% of a dry cell's mass by weight. In very broad and general terms, as cells mature and differentiate in the body, they reach an equilibrium in protein synthesis and protein degradation and settle down to perform their given function in this relative state of homeostasis. There are two notable exceptions that cause massive perturbations to this homeostasis: 1) when a cell is called upon to grow and divide and 2) when certain secretory cells are called upon to produce large amounts of proteins for secretion. Although the cell signaling signaling pathways, intracellular transduction pathways, and spectrum of protein(s) to be produced are quite different in growth versus secretion, normal growth and secretion events share one major similarity in their end result: massively accelerated protein synthesis. A cell that is called on to grow (cycling cell) has as much as 5 times the protein synthesis activity of a non cycling cell and needs between 2,000 and 5,000 different enzymes and structural proteins to grow and divide. Likewise, secretory cells such as those of the immune system become protein factories producing massive amounts of antibodies, mediators, growth factors, or other proteins when stimulated to do so.

There are also abnormal conditions such as cancer and viral infections that share the same property of hyperactive protein synthesis versus normal quiescent cells. Cancer is a growth and divide type event, and even though the signaling mechanism is different in that it is self-induced intracellularly by several genetic mutations, the end result is also hyperaccelerated protein synthesis characteristic of a cycling cell. Viruses invade a cell, parasitize the host cellular machinery, and convert the cell into a factory producing massive amounts of viral proteins, much like a secretory cell.

Inhibiting protein synthesis affects cells in a dose dependent manner and affects actively cycling cells differently than non cycling cells. At low doses, protein synthesis inhibitors (PSIs) stop actively cycling cells from cycling without killing them (hereinafter referred to as inhibitory or G zero inducing dose). Inhibitory doses also stop hyperaccelerated protein synthesis by secretory cells. At moderate doses PSIs exhibit toxicity to actively cycling cells (hereinafter referred to as the cytotoxic dose). At high doses, PSIs exhibit toxicity to all cells (hereinafter referred to as the toxic dose).

Psoriasis

Psoriasis presents as elevated lesions that vary in size between one to several centimeters.

Psoriasis is one of the most common dermatologic diseases, affecting about 2 percent of the population to some degree. There are actually several types of psoriasis, with plaque psoriasis being the most common, but the underlying problem in all of them is overproduction of epidermal cells. Instead of adhering to the 21 to 28 day cycle of cell turnover, those afflicted with psoriasis race through the cycle in 3 or 4 days. The epidermis may grow to 5 to 10 times its normal thickness. The thickened epidermis, overgrowth of blood vessels, and infiltrate of neutrophils and lymphocytes account for the psoriatic lesions being raised and easily palpable. The lesions may range from a few to many at any given time.

The etiology of psoriasis is still poorly understood, however evidence has accumulated clearly indicating a role for T cells. Hordes of activated T cells are found in psoriatic skin and almost none in healthy skin. It has also been discovered that these activated T cells secrete interleukin-6, which has as one of its effects the ability to stimulate skin cell growth. The infiltration of activated white blood cells suggest that an immune response has been mustered against something.

There are various theories about what that "something" is. One suggests a genetic abnormality as studies have shown concordant disease in 73% of monozygotic twins compared with 20% of dizygotic twins. The absence of 100% concordance among monozygotic twins suggests environmental factors must play a role. Other theories suggests that psoriasis is an immune system overreaction against invading organisms, or toxins produced by those organisms ("superantigens"), as it is known that latent psoriasis can be activated by various infections as well as certain drugs and injury to the skin. Bone marrow transplantation has resulted in clearance of the disease. In any event, psoriasis is currently considered to be an immunologic skin disorder.

Prior Art Treatments

Three basic treatment modalities are used under prior art: 1) topical agents, 2) phototherapy, and 3) systemic agents.

Topical Therapy—Outpatient topical therapy is the first-line approach. Several topical treatments are available, however no single ideal topical agent exists for plaque psoriasis. Topical treatments available are corticosteroids, coal tar, anthralin, calcipotriene, tazarotene.

Topical corticosteroids are considered the treatment of choice for the face, neck, skin folds, and genitalia for symptomatic relief. All topical steroids have anti-inflammatory, anti-pruritic, and vasoconstrictive effects. However their long term use is often accompanied by loss of effectiveness (tachyphylaxis). Systemic absorption is always a risk as it can suppress the pituitary-adrenal axis and induce cushingoid features.

Coal tar contains literally thousands of different substances and the exact mechanisms of action is unknown, though an antimitotic effect has been ascribed to these substances.

Anthralin is a synthetic derivative of a tree bark extract and in an antiproliferative agent that may upset oxidative metabolic processes, decreasing rate of epidermal cell proliferation. Although anthralin is considered one of the most effective agents available, it is not in widespread use because of high potential to cause irritation and staining.

Calcipotriene is a synthetic vitamin D-3 analog that regulates skin cell production however is not in widespread use because it is expensive and no more than 100 g/wk can be used because of the risk of irritation, hypercalcemia, and vitamin D toxicity.

Tazarotene is a retinoid derivative which very commonly causes irritation and as such is typically used in conjunction with a topical steroid. Retinoid derivatives alter the delayed hypersensitivity response and increase the number of Langerhans cells in the psoriatic lesion. Tazarotene is particularly useful for psoriasis involving the scalp. For plaque psoriasis, retinoids can be used in combination with ultraviolet phototherapy to minimize the dose of each.

Phototherapy—Phototherapy is generally used only in the presence of extensive, widespread disease. Resistance to topical treatments is another indication for phototherapy. There are two main forms of phototherapy; UVB and PUVA.

UVB or Ultraviolet B uses light in the 290–320 nm wavelengths and is usually combined with one or more topical treatments including; coal tar followed by UVB (Goeckerman regimen), tar bath followed by UVB followed by anthralin (Ingram method), or UVB combined with topical corticosteroids, calcipotriene, tazarotene, or simply bland emollients. A major drawback is the time commitment required and accessibility to UVB equipment. PUVA—uses the photosensitizing drug methoxsalen (8-methoxypsoralens) in conjunction with UVA light (wavelengths in the 320–400 nm range). PUVA interferes with DNA synthesis (methoxsalen binds covalently to pyrimidine bases in DNA), decreases cellular proliferation, and induces apoptosis of cutaneous lymphocytes leading to localized immunosuppression. Adverse effects include nausea, pruritus, burning, photo damage to the skin and increased risk of skin cancer.

Systemic Agents—Systemic Treatment is initiated only after both topical and phototherapy have failed or for patients with very active psoriatic arthritis. The main agents available are the immunomodulators Methotrexate and Cyclosporine and the oral retinoid Acitretin.

Methotrexate is a folic acid antagonist that inhibits DNA synthesis in tissues with high rates of turnover, such as psoriatic plaques, and is immunosuppressive to mononuclear cells in the skin, blood, and lymphatics. Methotrexate has toxic effects on hematologic, renal, GI, pulmonary, and neurologic systems.

Cyclosporine inhibits production of interleukin-2, the cytokine responsible for inducing T-Cell proliferation. Skin lesions recur within days to weeks after treatment is stopped. Adverse effects include hypertension, impaired renal function, and theoretically increased risk of cancer.

Acitretin is a second generation oral retinoid. The use of oral retinoid monotherapy has shown limited efficacy for chronic stable plaque psoriasis.

Harvey Lui, MD, FRCPC sums up the prior art situation well in the eMedicine Journal (Volume 2, Number 8): "No single ideal topical agent exists for plaque psoriasis." Compositions and methods of present invention will change that. The present invention provides topical compositions that have the ability to internalize rapidly into psoriatic tissue and inhibit virtually every aspect of psoriasis.

SUMMARY OF THE INVENTION AND NOVELTY OVER PRIOR ART

Novelty Over Prior Art Treatments of Psoriasis: Present invention overcomes the inability of prior art to provide a single topical agent for treatment of plaque psoriasis. It will be shown how compositions of present invention can be used to downregulate or shut down virtually every aspect of psoriasis. By binding to ribosomes and downregulating protein synthesis, it will be shown how compositions of present invention can be used to simultaneously; 1) directly stop cell cycling in basal layer epidermal stem cells (by dismantling the cell cycle control system), 2) directly stop cell cycling in endothelial cells (preventing angiogenesis), 3) depress production of growth factors underlying both epidermal and endothelial hyperactive growth, 4) depress activation of lymphocytes in response to antigens , and 5) retard maturation of differentiated epidermal cells.

Novelty and Unobviousness Over Prior Art Use of Trichothecene: Present Invention also overcomes prior arts inability to use trichothecene in treatment of hyperaccelerated growth conditions. Anguidine, a simple trichothecene, was tested against cancer and abandoned after Phase II testing showed a low tumor response and considerable hematologic toxicity. Prior arts attempt to remedy this failure are embodied in U.S. Pat. Nos. 4,906,452 and 4,744,981 which propose conjugates of trichothecene with monoclonal antibodies to enhance delivery to the tumor and glycosylation of trichothecene to increase blood solubility. Present invention takes a novel and unobvious approach that is exactly opposite to prior art in several respects. First, present invention reverses direction of administration (i.e. administered from tissue side to blood versus prior arts direction of blood to tissue). Second, present invention embraces the non specific internalization properties to deliver the greatest doses to tissues it is applied to and depending on those tissues to retain the trichothecene, preventing it from reaching general circulation (versus prior arts targeted delivery by monoclonal antibodies). Third, present invention embraces the use of macrocyclic trichothecene (versus simple trichothecenes in prior art) because the macrocyclic ring enhances rapid non specific internalization further enhancing localization and preventing entry into the blood. Fourth, present invention embraces blood insolubility to prevent entry into the blood (versus prior art glycosylation). Last, present invention uses inhibitory (non toxic) doses (versus prior arts toxic doses) and works primarily by dismantling the cell cycle control system versus killing the cell.

BRIEF DESCRIPTION OF DRAWING FIGURES

Figures 1A, 1B:
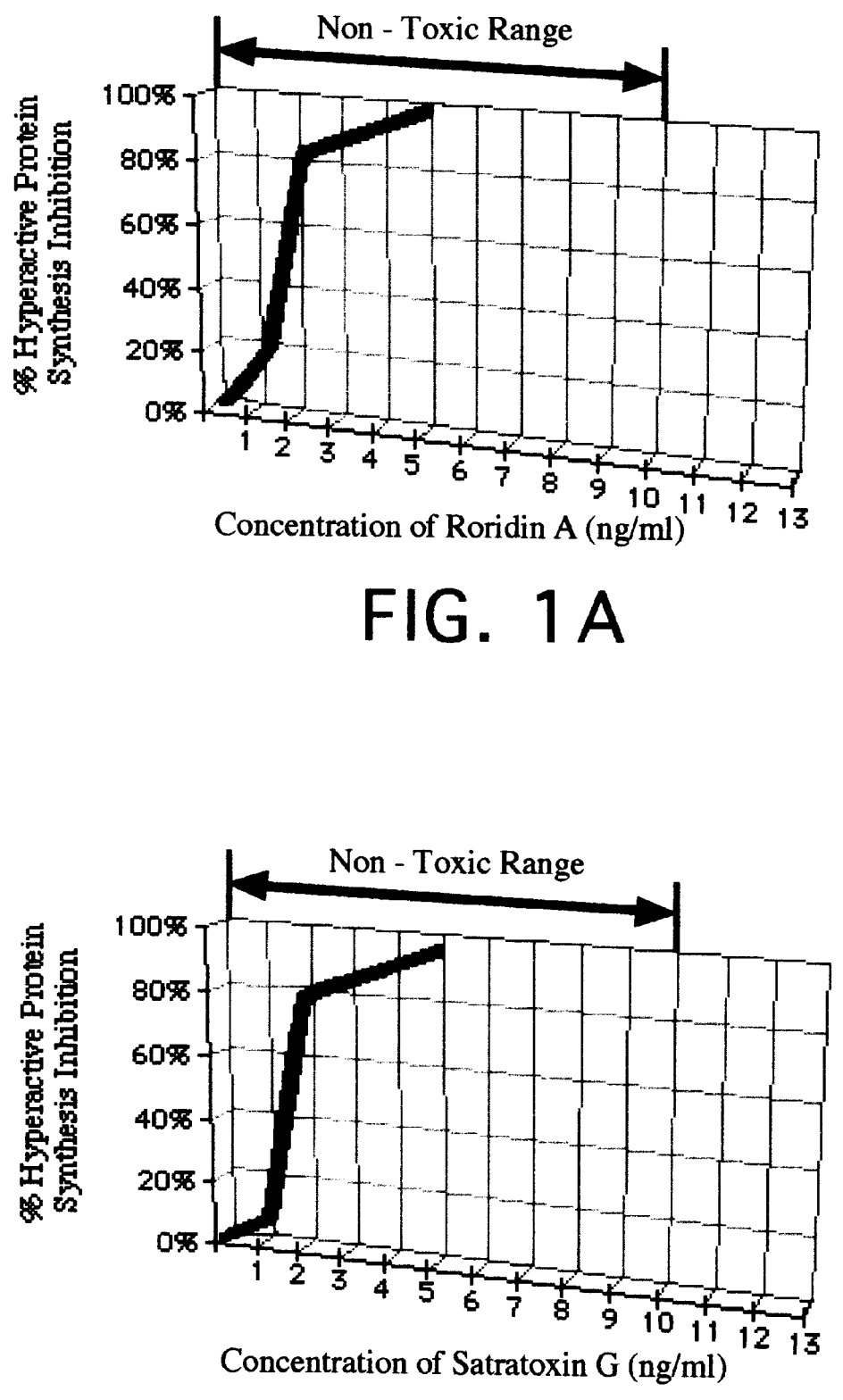

FIG. 1A shows the hyperactive protein synthesis inhibiting dose profile in human epidermoid cells of Roridin A, a representative macrocyclic trichothecene.

FIG. 1B shows the hyperactive protein synthesis inhibiting dose profile in human epidermoid cells of Satratoxin G, a representative macrocyclic trichothecene.

FIG. 2A shows the hyperactive protein synthesis inhibiting dose profile in human epidermoid cells of T-2, a representative simple trichothecene.

FIG. 2B shows the hyperactive protein synthesis inhibiting dose profile in human epidermoid cells of DAS, a representative simple trichothecene.

FIG. 3 shows the hyperactive Cyclin/CDK protein synthesis activity required at various points in the cell cycle to drive the cell through the cell cycle (i.e. the cell cycle control system).

FIG. 4 shows the molecular pathways depending on the hyperactive protein synthesis of the G1 cyclin/CDK proteins required to drive the cell through the G1 phase of the cell cycle.

DETAILED DESCRIPTION OF THE INVENTION

The treatments disclosed below involve topical administration of biologically active trichothecenes the effectuate the inhibition of psoriasis by several mechanisms of action targeted at several target cell populations of both the epidermis and immune system. Materials and methods for achieving this are described below.

Trichothecenes Defined

Fungi of the genera Fusarium, Myrotecium, Trichoderma, Stachybotrys and others produce Trichothecene mycotoxins. Trichothecenes constitute a family of fungal sesquiterpene epoxides that inhibit protein synthesis. Trichothecene mycotoxins are low molecular weight (250–700 daltons), non volatile compounds, and of over 150 trichothecenes have been identified. There are two broad classes: those that have only a central sesquiterpenoid struct or molecules of the following general formula:
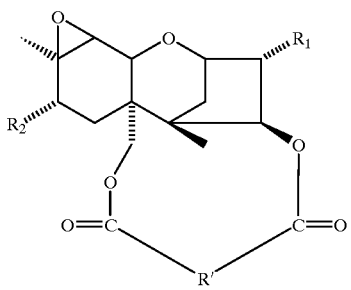

Wherein $R_1$ is H, OH or

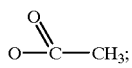

$R_2$ is H, OH,

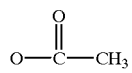

or $OCOCH_2CH(CH_3)_2$; and

R' is any molecule composed predominantly, or in its entirety, of combinations of C, H, and O.

A more comprehensive listing of trichothecenes is included in U.S. Pat. Nos. 4,744,981 and 4,906,452, incorporated herein by reference.

Trichothecenes are fast acting potent inhibitors of protein synthesis in eucaryotic cells. Their main effects are on rapidly proliferating tissues such as bone marrow, skin, mucosa epithelia, and germ cells. The sesquiterpenoid ring binds to ribosomes, inhibiting protein synthesis. The macrocyclic ring enhances cell binding and internalization.

Trichothecenes are invisible to the immune system since they neither contain nor produce amino acids. Since trichothecene molecules contain only carbon, hydrogen, and oxygen they are not subject to proteolytic degradation. U.S. Pat. No. 4,906,452 (column 11 first paragraph) further discloses that some studies of the rates at which certain trichothecenes are converted into biologically inactive molecules (apotrichothecenes) found that macrocyclic trichothecenes are inactivated quite slowly and only by intracellular acid catalysis as might occur in lyzosomes.

Trichothecenes are extremely stable to heat and ultraviolet light inactivation. Heating to 500° F. for 30 minutes is required for inactivation. Brief exposure to NaOH destroys toxic activity. These substances are relatively insoluble in water but are highly soluble in ethanol, methanol, and propylene glycol.

Trichothecene's Mechanisms of Action in Preventing Psoriasis

Present invention intends to overcome prior arts inability to provide a single ideal topical agent for plaque psoriasis by providing a composition that simultaneously works by several mechanisms of action to shut down virtually every pathway involved in psoriasis. The pathways inhibited are:

Inhibiting the Cell Cycle Control System—Low doses of protein synthesis inhibitors stop actively cycling cells from cycling (without killing them). It has been shown that briefly inhibiting protein synthesis in early G1 (MBOC 896–897) stops cells from cycling by dismantling the cell cycle control system. After inactivation of the protein synthesis inhibitor, the cells require roughly 8 hours to rebuild their cell cycle control system and start cycling again.

A cycling cell is driven by an orderly sequence of events coordinated by the cell cycle control system. The cell cycle control system is dependent on hyperactive burst of protein synthesis of cyclins and cyclin dependent kinases (CDK). FIG. 3 shows the bursts of cyclin/CDK protein synthesis required to drive a cell through the various parts of the cell cycle. FIG. 4 shows the cell cycle control systems pathways involved in driving a cell through the G1 phase of the cell cycle. In a typical cell, inhibitory influences predominate and the normal state of a cell is not to cycle. In the non cycling cell, the Rb protein is bound to the E2F-DP1 transcription factor inhibiting it. When stimulated to proliferate, hyperactive protein synthesis of Cyclin/CDK is initiated, in particular Cyclin D/CDK4/6 complexes and Cyclin E/CDK2 complexes in G1, which phosphorylate the Rb protein, inactivating it, in turn activating the E2F-DP1 transcription factor. Inhibiting hyperactive protein synthesis of cyclins and CDKs prevents a cell from cycling. Cyclins such as cyclin D have short half lives (~15 minutes for cyclin D) and inhibiting their synthesis reduces their concentrations rapidly. After inactivation of the protein synthesis inhibitor, the cell requires 8 or so hours to rebuild its cyclin/CDK levels before it can resume cycling again. The inactivation period of certain trichothecenes, however, can be very long—on the order of 10 days or more—as discussed later in this application.

Inhibition of Angiogenesis—Psoriasis also involves another process that is dependent on hyperactive protein synthesis and hyperactive cell proliferation: angiogenesis. Angiogenesis is the growth of new blood vessels. Without angiogenesis a tissue mass cannot grow beyond the size of a pinhead (~1 to 2 cubic millimeters). The naturally occurring balance between stimulators and inhibitors of angiogenesis in the human body is also one in which inhibitory influences predominate. The rare instances in which angiogenesis occurs under normal conditions are wound healing, organ regeneration, embryonic development, and female reproductive processes. Also, when cells are deprived of oxygen or nutrients, they produce and release angiogenic factors (proteins) that induce new capillary growth which is why nearly all vertebrate cell are located within 50 $\mu$m of a capillary. Unnatural or disease conditions that involve angiogenesis include psoriasis. Angiogenic growth factor protein production can come directly from epidermal cells as they crowd each other or from immune system mediated processes. Protein growth factors for angiogenesis dock with growth factor receptors on nearby endothelial cells (cells that form the wall of blood vessels). A normally dormant endothelial cell becomes activated, secretes enzymes that degrade the extracellular matrix (the surrounding tissue), invades the matrix, begins dividing and eventually the new endothelial cells organize into hollow tubes creating new networks of blood vessels.

Trichothecene administration would directly inhibit angiogenesis by dismantling the cell cycle control system in endothelial cells by the same Cyclin/CDK mechanisms described for epidermal cells.

Inhibiting Overexpressed Growth Factors—Trichothecenes, as a preferential inhibitor or hyperactive protein synthesis, would also inhibit overexpression of growth factor proteins for both epidermal proliferation and angiogenesis. It would locally inhibit the excessive production of protein growth factors, regardless of which cells they originate in (i.e.. T-Cell produced interleukins or epithelial growth factors produced by crowded/starved epidermal cells).

Immunosuppression—The immune response is also mediated by hyperactive protein synthesis. Trichothecenes are known to be immunosuppressive by virtue of their ability to inhibit protein synthesis and would thus also locally depress T-Cell or B-Cell responses to antigens (i.e. the previously mentioned "something" that triggers the immune response to begin with).

Retarding Maturation of Differentiated Cells—The epidermis grows from the bottom up, starting with basal cells (only these undergo mitosis) which divide and then mature into prickle cells, granular cells, and eventually squames. Transformation is a highly protein driven event and retarding protein synthesis would also retard the maturation of differentiated cells, retarding the "racing through the cycle" observed in psoriasis.

Preferred Trichothecenes

Macrocyclic trichothecenes are preferred for use in present invention because they are relatively insoluble in blood and because the macrocyclic ring enhances cellular binding and internalization which tends to localize them more quickly and prevent their entry into general circulation.

An excellent in vivo example of this is the Cleveland Infant Model. Although present invention deals with much lower inhibitory doses, even at much higher cytotoxic doses, with ruptured blood vessels in the vicinity, the Cleveland infant model showed the reluctance of macrocyclic trichothecenes to enter the blood stream, and instead their tendency to localize into the epithelium with which they initially came into contact with.

The Cleveland Infant Model: The cluster of infant hemosiderosis in Cleveland (MMWR report) demonstrated, in vivo, in humans, the ability of certain macrocyclic trichothecenes to localize in tissue without appreciably entering general circulation. Adults and infants were subjected (inadvertently) to airborne (cytotoxic) concentrations of trichothecenes produced naturally by the fungus Stachybotrys atra. Trichothecenes produced by S. Atra include satratoxins H, G, F, roridin E, verrucarin J, and trichoverrols A and B.

The mean age of the infants was ~10 weeks old (range 4–16 weeks). At this age, the lungs of infants are growing at an accelerated rate, and the destruction of lung tissue clearly indicated cytotoxic airborne concentrations (versus the lower inhibitory ones used in present invention). The median age of the infant's mothers was 20 years (range 15–29 years). At this age, the lungs of adults are not growing at an accelerated rate, and are thus not affected by the cytotoxic dose levels. No serious health problems were reported by the adults.

In the infants examined, despite the acute pulmonary hemorrhage/hemosiderosis, the inhaled trichothecenes localized in the lung epithelium and did not enter circulation where they would have caused systemic cytotoxicity. Laboratory findings on admission showed a normal white blood cell count (median=13.8 cells/cubic mm) in the infants. Red blood cell counts were consistent with the blood loss from the hemosiderosis. No other source of bleeding (i.e. gastrointestinal or nasopharyngeal) was identified during endoscopic evaluation. This demonstrates both the reluctance of these macrocyclic trichothecenes to enter the blood stream as well as the tendency for them to localize into the epithelium with which they first came into contact with.

The likely molecular basis for the "localization" of these trichothecenes is their ability to be rapidly internalized into cells because of their macrocyclic ring combined with their insolubility in blood, which would tend to keep them out of the circulatory system. The incredibly small size of trichothecenes (~1 nm or less) allows them to travel between cells (~2–4 nm spacing). Once internalized they can travel through gap junctions. Gap junctions allow molecules smaller than 1000 daltons (~1.5 nm in diameter) to pass between connected cells and trichothecenes are comfortably under the size limitation at 250–700 daltons. Gap junction travel would tend to further localized trichothecenes within the organ or other connected tissue mass.

It is likely the inhaled trichothecenes are somewhat "trapped" between the lumen of the lungs on one side and the circulatory system on the other side, in which they are insoluble. In between this is the lung tissue in which they eventually internalized—in virtually the same way they would be expected to act when applied topically to the skin—internalizing in the skin without appreciably entering general circulation.

Although there have been studies on the rates at which trichothecenes are intracellularly converted into biologically inactive apotrichothecenes, the Cleveland infant model also provides a rare glimpse of how slowly macrocyclic trichothecenes are inactivated, in vivo. All infants survived the first hospitalization and were discharged without evidence of hemoptysis after a median length of stay of 10 days, indicating an inactivation time in the ballpark of 10 days.

Preparation of Trichothecenes

Fungi can be grown in culture and the trichothecenes extracted by centrifugal partition chromatography as described in Tani et. al. and described in other literature such as Onji et. al. (Onji, Y., Aoki, Y., Yamazoe, Y., Dohi, Y., and Mornyamam, T., 1988 Isolation of nivalenol and fusarenon-X from pressed barley culture by centrifugal partition chromatography, Journal Liquid Chromatography, 11:2537–2546) or Jarvis et al. (Jarvis, B. B., R. M. Eppley, and E. P. Mazzola, 1983 Chemistry and Bioproduction of the Macrocyclic Trichothecenes, p 20–38. In Y. Ueno, Trichothecenes: chemical, biological, and toxicological aspects, vol 4. Elsevier Science Publishing Inc., New York) or Sorensen et al. (Sorenson, W. G., Frazer, D. G., Jarvis, B. B., Simpson, J., and Robinson, V. A., Trichothecene Mycotoxins in Aerosolized Conidia of Stachybotrys atra, June 1987 Applied and Environmental Microbiology, Vol. 53 No. 6, p. 1370–1375) where S. atra was grown on sterile rice, autoclaved, dried, and then aerosolized by acoustic vibration and collected on glass-fiber filters and extracted with 90% aqueous methanol.

Alternatively, certain trichothecene mycotoxins can be purchased from companies such as Sigma Chemical Co. St. Louis Mo., USA or Wako Pure Chemical Industries, Ltd., Japan, or Wellcome Research Labs, Buckinghamshire, England or Boehringer-Mannheim, Manheim, West Germany.

Method of Administration

Preferred embodiment of current invention administers trichothecenes by topical application, mixed with either ethanol, methanol, propylene glycol, or dimethyl sulfoxide. The latter serve no biological role other than to act a vehicle to facilitate uniform distribution of the trichothecene to a given area of skin. These mixtures are hereinafter referred to as "therapeutic compositions" or "pharmaceutical compositions" or "compositions" and nothing in this application is intended to limit trichothecene from being mixed with any suitable substance that may facilitate administration, uniformity of distribution, enhance absorption, increase efficacy, or with other trichothecenes or any other substances that serve any other beneficial purpose, the aforementioned combinations also called "therapeutic composition" or "pharmaceutical compositions" of present invention. The term "therapeutics" or "therapeutics of present invention" is generally intended to refer to the biologically active trichothecene(s).

Dose Determination

Two broad methods may be employed in treating Psoriasis: Full Inhibition or Partial Inhibition. The dose varies with the method used.

Full Inhibition—A therapeutically effective dose of trichothecene as proposed in present invention under Full Inhibition is defined as a dose of the toxin that completely inhibits epidermal cell growth in psoriasis. The effective dose is expressed as the ~100% psoriatic inhibitory concentration ($PIC_{100}$) which is the concentration required to completely inhibit cell cycling without inducing toxicity to the epidermal skin population. Intermittent administration returns psoriatic skin back to normal by periodically discontinuing administration (i.e. 3–4 day drug inactive period) so that even though the skin still races through the complete cycle in 3 to 4 days, it is allowed to do so only once a month, thus approximating the normal one complete cycle per month of normnal skin. $PIC_{100\ min}$ is hereby defined as the minimum concentration that inhibits ~100% of psoriatic cell growth without inducing toxicity to epidermal skin cells. $PIC_{100\ max}$ is hereby defined as the maximum concentration that inhibits ~100% of psoriatic cell growth without inducing toxicity to epidermal skin cells.

Partial Inhibition—A therapeutically effective dosage of trichothecene as proposed in present invention under Partial Inhibition is defined as a dose of the toxin that inhibits epidermal cell growth in psoriasis to a level that is normal in the absence of the condition. The effective dosage of each specific toxin is expressed as the approximately 85% psoriatic inhibitory concentration ($PIC_{85}$) which is the concentration required to reduce psoriatic cell growth by 85%. The underlying abnormality in psoriasis is that skin cells race through the process approximately 7 times faster than normal and, mathematically, an approximately 85% psoriatic inhibitory concentration ($PIC_{85}$) would inhibit the accelerated process to bring it back in line with normal cell growth rates (i.e. reducing the process from 7× to 15% of 7×~1, the normal skin maturation rate). The range of accelerated skin growth can vary by individual from 5 to 10 times faster, which mathematically, would imply a range of $PIC_{80}$ to $PIC_{90}$ for most patients.

Therapeutics, containning $PIC_{80}$, $PIC_{85}$, $PIC_{90}$ would provide physicians with the ability to more closely match patient needs however nothing in this application should be construed to limit other embodiments to any PIC value that subsequently may be found of therapeutic use. Continuous Administration as used in this application should not be construed to mean "daily" but once per time period required to maintain efficacy (i.e. dependent on intracellular inactivation time), and in the case of certain trichothecenes chosen, may mean once every 10 days or so.

Figures 2A, 2B:
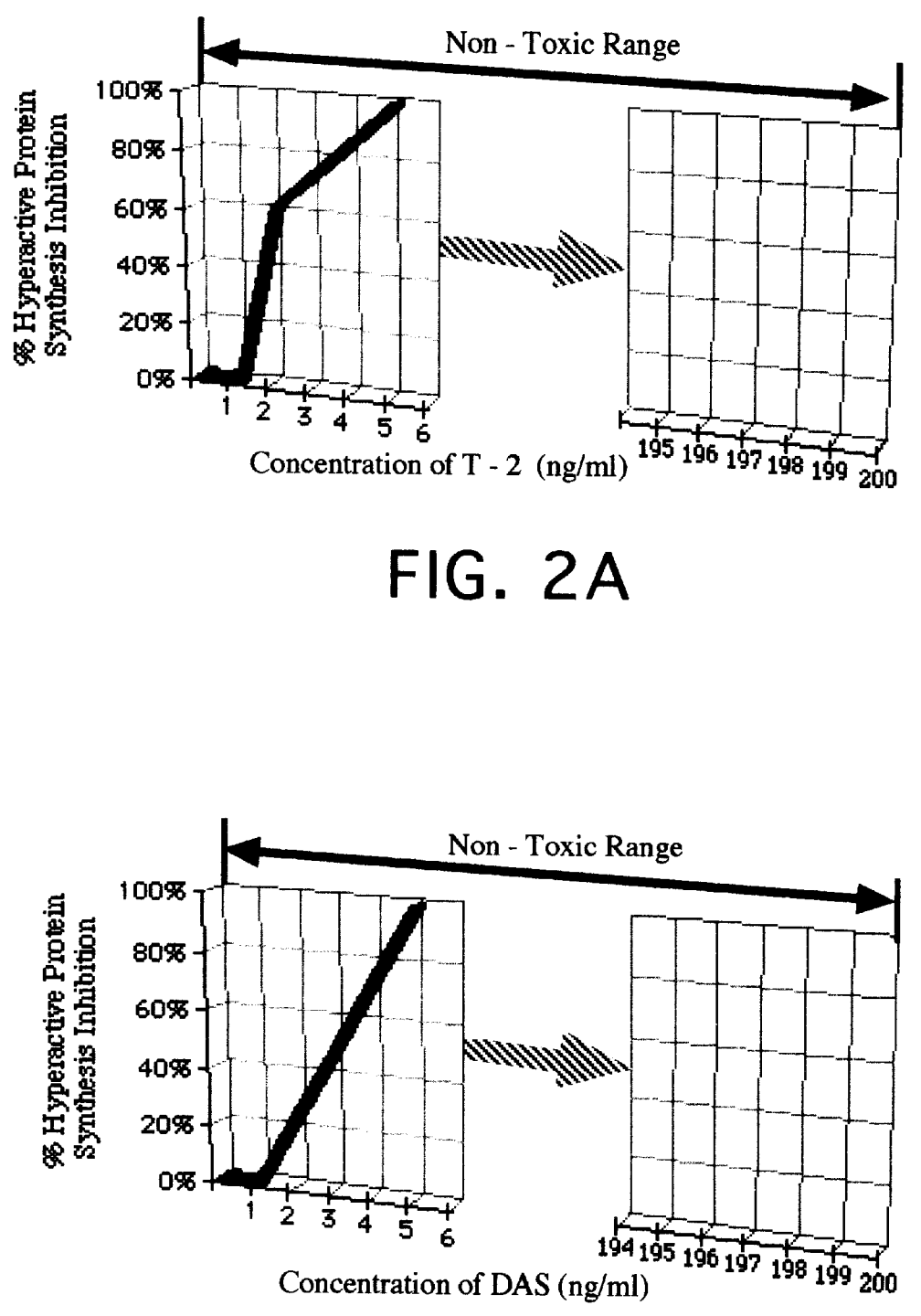

The $PIC_{80}$, $PIC_{85}$, $PIC_{90}$, $PIC_{100}$ and $PIC_{100\ max}$ for four representative trichothiecenes are presented below. The hyperactive protein synthesis inhibiting profiles were constructed from data collected from in vitro experiments using human epidermoid cells, virally infected with HSV-2 to induce a hyperactive state of protein synthesis, and conducted and reported by Okazaki et. al. in the attached Journal of Agricultural and Biological Chemistry articles. Since the Okazaki experiments were to determine viral inhibition properties, the data has been reformatted for relevance to present application of inhibiting hyperactively cycling cells. Stated data points were taken from Okazaki's text, other data points were read from the graph, the rest were computed by linear interpolation between the aforementioned data points. FIGS. 1A and 1B show the hyperactive protein synthesis inhibiting dose profile of roridin A and satratoxin G, respectively. Both roridin A and satratoxin G are macrocyclic trichothecenes. By ~5 ng/ml both had inhibited almost 100% of the hyperactive protein synthesis. Both did not reduce cell viability at concentrations of 10 ng/ml or less (i.e. $PIC_{100\ max}$). FIGS. 2A and 2B show the hyperactive protein synthesis inhibiting dose profile of T-2 and DAS, respectively. Both T-2 and DAS are simple trichothecenes. By doses of 5 ng/ml both had inhibited ~99% of hyperactive protein synthesis. Neither reduced cell viability at concentrations up to 200 ng/ml (i.e. $PIC_{100\ max}$). TABLE 1 summarizes concentrations relevant to the inhibitory levels previously defined.

TABLE 1

| | Trichothecene Concentrations (ng/ml) | | | | | |
|---|---|---|---|---|---|---|
| | Protein Synthesis Inhibition | | | | | |
| | 50% | 80% | 85% | 90% | $PIC_{100}$ | $PIC_{100\ max}$ |
| Roridin A | 1.4 | 2.0 | 2.5 | 3.3 | 5.0 | 10 |
| Satratoxin G | 1.5 | 2.4 | 3.2 | 3.9 | 5.0 | 10 |
| T-2 | 1.6 | 3.5 | 3.8 | 4.3 | 5.0 | 200 |
| DAS | 2.3 | 4.0 | 4.2 | 4.5 | 5.0 | 200 |

Conversion of in vitro concentrations to dosages required to achieve in vivo epidermal concentrations would be performed by simple mathematical methods to achieve the desired concentrations in a given volume of skin. Normal epidermis is ~200 µm thick. Psoriasis can cause the epidermis to thicken from 5 to 10 times normal thickness or from 1 mm (hereinafter referred to as moderate thickness psoriasis) to 2 mm (hereinafter referred to as extreme thickness psoriasis). The volume of epidermis per square centimeter of skin surface area can thus range from 20 cubic mm for normal epidermal thickness (10 mm×10 mm×0.2 mm) to 100 cubic mm for moderate thickness psoriasis (i.e. 10 mm×10 mm×1 mm) to 200 cubic mm for extreme thickness psoriasis (i.e. 10 mm×10 mm×2 mm). Converting these volumes to ml at a rate of 1 cubic mm=1/1000 ml gives the respective volumes in ml as 0.02 ml per square cm of skin surface area for normal epidermal thickness (i.e. 20 cubic mm/1000), 0.1 ml per square cm of skin surface area for moderate thickness psoriasis (i.e. 100 cubic mm/1000) and 0.2 ml per square cm of skin surface area for extreme thickness psoriasis (i.e. 200 cubic mm/1000). The absolute amount of trichothecene to be administered per square cm of skin surface area to achieve the desired $PIC_{100}$ concentration of 5 ng/ml can now be computed; 0.1 ng per square cm of skin surface area for normal thickness skin (i.e. 0.02 ml×5 ng/ml=0.1 ng), 0.5 ng per square cm for moderate thickness psoriasis (i.e. 0.1 ml×5 ng/ml=0.5 ng) and 1 ng per square cm for extreme thickness psoriasis (i.e. 0.2 ml×5 ng/ml=1 ng). As an example, if a patients has a psoriatic patch of skin of ~1 square centimeter and it is 1 mm thick and one desires to achieve a $PIC_{100}$ concentration of 5 ng/ml of Satratoxin in the epidermis one would need to topically apply 0.1 ml of a solution such as ethanol possessing a concentration of 5 ng/ml of trichothecene (when the ethanol evaporates it leaves 0.5 ng in the 0.1 ml of epidermis or 5 ng/ml). The concentration of the topical solution can be varied as desired as long as it leaves 0.5 ng of trichothecene per square cm of epidermis to which it is topically applied (i.e. 0.1 ml of 5 ng/ml trichothecene solution can be substituted with 0.25 ml of 2 ng/ml solution, 0.05 ml of 10 ng/ml solution etc . . . ) Likewise if the psoriatic epidermis is extremely thick such as 2 mm (i.e. 0.2 ml skin volume) the dose is proportionately computed so that 1 ng needs to be administered per square centimeter of psoriatic epidermis. Once the epidermal thickness has returned to normal the "maintenance mode" dose requires only 0.1 ng per square cm, of epidermis. TABLE 2 provides some examples of dosaging guidelines calculated by the method described above.

TABLE 2

$PIC_{100}$ Dose Table for Satratoxin, Roridin, T-2, and DAS
($PIC_{100}$ = 5 ng/ml of skin volume)

| Epidermal Thickness (mm) | Epid. Vol. /sq cm skin | ng to = $PIC_{100}$ | 2 ng/ml Solution | 5 ng/ml Solution | 10 ng/ml Solution |
|---|---|---|---|---|---|
| .2 (normal skin) | .02 ml | 0.1 ng | .05 ml | .02 ml | .01 ml |
| 1 (moderate psoriasis) | .10 ml | 0.5 ng | .25 ml | .10 ml | .05 ml |
| 2 (extreme psoriasis) | .20 ml | 1.0 ng | .50 ml | .20 ml | .10 ml |

Likewise the $PIC_{80}$, $PIC_{85}$, and $PIC_{90}$ levels can be computed. TABLE 3 shows the $PIC_{85}$ for the representative trichothecenes and the corresponding dose in ng/sq cm of epidermis to achieve $PIC_{85}$. As previously shown, different combinations of concentrations and amounts of solution may be used to administer these doses.

TABLE 3

$PIC_{85}$ Dose Table

| Trichothecene | $PIC_{85}$ | Corresponding Dose of Trichothecene in ng/sq cm of epidermis @ various skin thicknesses | | |
|---|---|---|---|---|
| | | .2 mm | 1 mm | 2 mm |
| Roridin A | 2.5 ng/ml | .050 ng | .25 ng | .50 ng |
| Satratoxin G | 3.2 ng/ml | .064 ng | .32 ng | .64 ng |
| T-2 | 3.8 ng/ml | .076 ng | .38 ng | .76 ng |
| DAS | 4.2 ng/ml | .084 ng | .42 ng | .84 ng |

There are many variants on dosaging schemes however one merits further discussion because of its potential application as a self administered home treatment method. Dosage level is also interchangeable with frequency of administration. In vivo inactivation times for certain macrocyclic trichothecenes are in the order of 10 days as previously discussed. Lower doses, more frequently applied, to attain and maintain the defined epidermal $PIC_{85}$ or $PIC_{100}$ levels could be used in self administration regimens while providing a comfortable degree of safety. As an example a $PIC_{85}$ concentration, given a 10 day inactivation time, can be achieved in one application every 10 days, or alternatively it can be achieved by daily administration of the same amount of solution containing one tenth the concentration or using the same concentration but applying one tenth the amount of solution. Using lower doses and higher frequency of administration to achieve the cumulative epidermal concentrations outlined in the dose determination section above may actually be preferable in more evenly inhibiting some of the more mobile cells such as those of the immune system. The possible combinations of dosaging regimens to achieve the PIC levels defined in this application are innumerable and the examples presented in this application are only a few representative examples.

Figure 4:
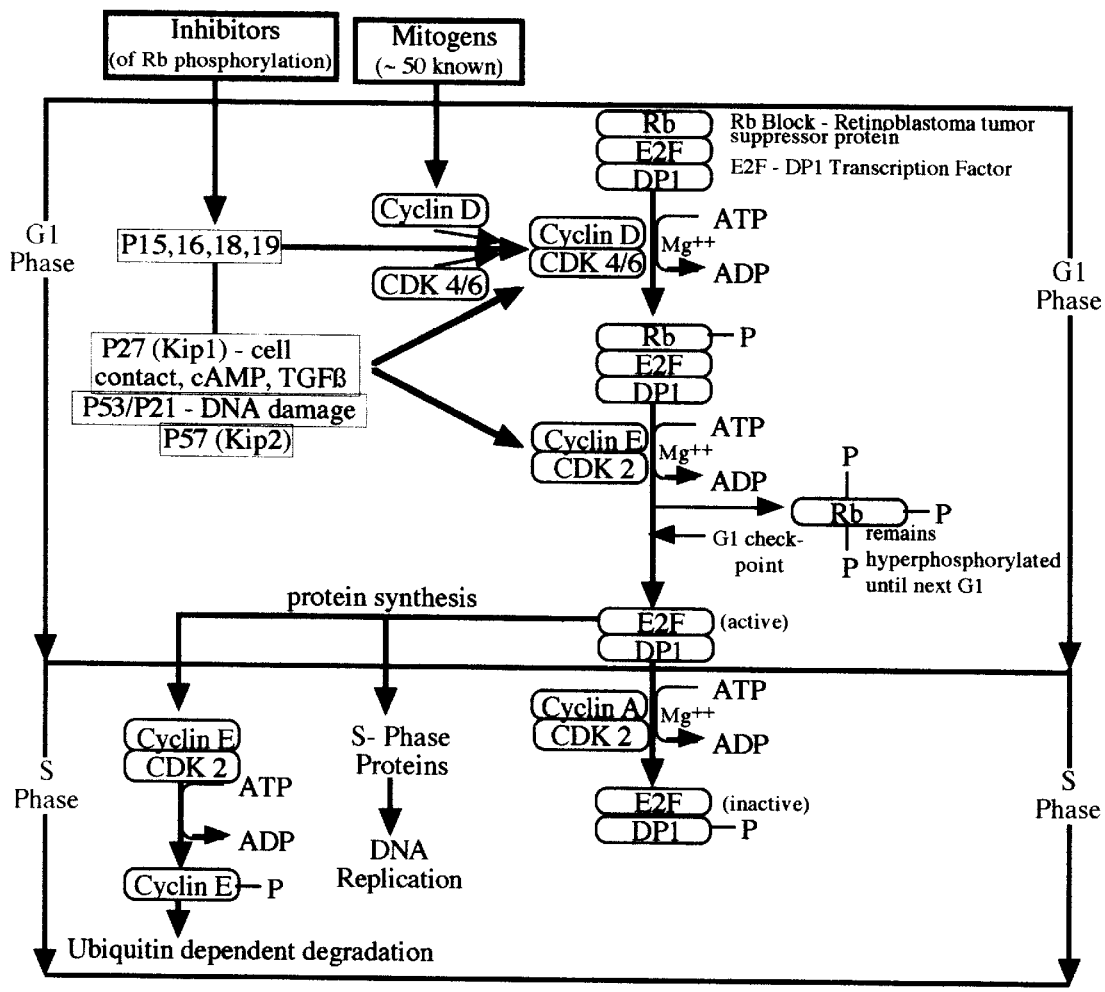

It should be noted that a "drug inactive" period would also be required for $PIC_{85}$ doses, similar to the 3–4 days per month for $PIC_{100}$. This is because although $PIC_{85}$ would depress ~85% of protein synthesis, proportionately slowing down maturation of differentiated cells, growth factor production, and immune response, it would completely inhibit new epidermal cell division. The cell cycle control system is a "all or nothing" system and as shown in FIGS. 3 & 4, driven by rapid burst of protein synthesis that need to reach critical concentrations to drive the cell forward through the cell cycle. 85% protein synthesis inhibition translates into 100% cell division inhibition.

It should also be recognized that, from a practical standpoint, more solution may need to be administered than presented in the examples to achieve the desired PIC epidermal concentrations defined in present application. In the examples, the amount of trichothecene contained in the solution administered was set to match the dose required for the given epidermal volume for the sake of clarity. As is customary under prior art, all dosages would be further refined and scrutinized by in vivo testing in suitable animal models or in Phase I and II clinical trials on humans as required by the FDA.

Lastly, the goal of achieving the ideal epidermal depth of 200 $\mu$m is not an absolute. Reducing psoriatic epidermis from 1 or 2 mm to 400 $\mu$m (twice normal epidermal depth) may be a very acceptable treatment regimen. It simplifies administration to twice monthly, allowing 2 full epidermal cycles per month versus 1 and may be visually imperceptible relative to normal skin.

Given the above Tables and computations some simple examples of treatments are presented below.

TREATMENT EXAMPLES

Example 1

A patient presents with a psoriatic lesion of ~10 square centimeters on their arm and it is ~1 mm thick. Treatment: The psoriatic lesion is slightly abraded with a pumice stone, defatted with Acetone, and petroleum jelly is placed on the normal skin around the psoriatic lesion. The patient is given a $PIC_{100}$ dose of 5 ng of satratoxin in ethanol which is topically administered to the psoriatic lesion (e.g. by eye dropper, needless syringe, or any other suitable means). This procedure is repeated in alternating cycles of 10 days, 14 days, 10 days, 14 days etc . . . (or any other suitable time period).

Example 2

A patient presents with a psoriatic lesion of ~10 square centimeters on their arm and it is ~1 mm thick. Treatment: The patient is given a $PIC_{85}$ dose 2.5 ng roridin in propylene glycol which is topically applied to the psoriatic lesion (e.g. by brush, q-tip, or any other suitable means). The procedure is repeated as in example 1, or at any other suitable time period.

Example 3

A patient presents with a psoriatic lesion of ~10 square centimeters on their arm and it is ~1 mm thick. Treatment: The patient is given a $PIC_{100}$ dose comprising 2.5 ng of satratoxin and 2.5 ng of T-2 in an ethanol solution. Treatment is repeated as in example 1.

Example 4

A patient had a psoriatic lesion of ~10 square centimeters on their arm has been treated several times and the epidermis has returned to a normal thickness of ~0.2 mm. The patient is given a topical cream containing 5 ng/ml of any one of the 4 trichothecenes presented and instructed to apply 0.2 ml (i.e. the $PIC_{100}$) to the psoriatic area once every 14 days thereafter (or any other suitable time period if the epidermis starts to thicken sooner). The patient is advised to immediately discontinue use and see the physician if the epidermis starts to thin or any redness is observed (i.e. psoriasis has gone away for good).

Example 5

A patient had a psoriatic lesion of ~10 square centimeters on their arm that has been treated and the epidermis has returned to a normal thickness of ~0.2 mm. The patient is instructed to, once a day, apply 1 ml of a cream containing 0.05 ng/ml of roridin (i.e. 10% of $PIC_{85}$ dose; PIC85=0.05 ng/sq cm for normal thickness epidermis×10 sq cm=0.5 ng total dose) to the psoriatic area for ~3 weeks then discontinue using it for ~1 week, continuing the 3 week "on" 1 week "off" cycle thereafter as necessary. The patient is advised to immediately discontinue use and see the physician if the epidermis starts to thin or any redness is observed.

Preferred embodiment of present invention favors use of macrocyclic trichothecenes because the macrocyclic ring enhances cellular internalization, localizing more of the therapeutics in the epidermis and reducing transdermal migration into the blood stream. However nothing in this application or its related claims should be construed to limit use of simple trichothecenes or combinations of macrocyclic and simple trichothecenes. As an example, a combination of 0.5 ng Satratoxin and 0.5 ng of T-2 per 1 ml of therapeutic could be used and be more efficacious than 1 ng of either alone as the macrocyclics would internalize more rapidly (higher concentration in upper layers) and the simple trichothecenes would penetrate deeper, concurrently the two could provide more uniform distribution through both upper and lower layers of the epidermis.

Present invention also envisions possible preparation of skin prior to administration of therapeutics of present inventions is also envisioned. Several pretreatment methods exist to facilitate deeper and more even distribution of substances and these generally involve removal of some of the uppermost portions of the epidermis. A simple mechanical removal of some of the outermost layers of psoriatic skin may be performed by simple mechanical abrasion with a pumice stone or loofah sponge. Alternatively, substances such as alpha of beta hydroxy acids may be applied prior to application of therapeutics. These acids dissolve the intercellular glue that hold cells together, allowing for better penetration of therapeutics of invention. Various types of alpha hydroxy acids (including lactic acid, citric acid, and glycolic acid) act in the upper layers of the epidermis to dissolve the intercellular glue. Beta hydroxy acid work in deeper layers of the epidermis. Lack of cellular attachment would facilitate profusion on therapeutic in the epidermis. Defatting skin with acetone prior to administration of therapeutics is used to facilitate uniform distribution of therapeutics.

Present invention also envisions directly incorporating any other substances into pharmaceutical compositions of present invention, such as those mentioned above that may facilitate application, enhance delivery or uniformity of distribution, or in any way increase efficacy into therapeutic compositions of present invention, including adding substances currently in use for topical treatment of psoriasis that function by alternative mechanisms of action or complementary mechanisms of action, previously described under prior art treatments section of this application, or any new such drugs to come onto the market in the future.

Nothing in this application is intended to limit additional compositions that may be added to or used in conjunction with pharmaceutical composition of present invention. Although therapeutics of present invention may be topically administered in any suitable solution (e.g. ethanol, methanol, propylene glycol, dimethyl sulfoxide) any other suitable agent, carrier or delivery vehicle may be use. A wide variety of compositions including antibiotics, antibiotic creams, or non-toxic pharmaceutical carriers or vehicles KY Jelly, or the like, and in any suitable form such as a liquid, solid, semi-solid, ointment, lotion, paste, or the like may also be used where advantageous. Heavier creams are specifically envisioned for home use type applications to make "idiot proof" pharmaceutical compositions that limit the dose of therapeutic that may be administered to a given area of skin.

Nothing in the application is intended to limit the devices and methods used to facilitate application or either therapeutics or pharmaceutical compositions of present invention. The examples of devices presented are only representative examples. Other devices, either currently existing, or to be developed in the future could also be employed. As an example devices (e.g. low velocity "atomizers") capable of accelerating therapeutics or pharmaceutical compositions of present invention to velocities capable of instantaneous epidermal penetration and distribution would in fact be a preferred delivery method in many applications.

Safety by Topical Administration

As previously mentioned trichothecenes affect different cells in a dose dependent manner: at inhibitory doses they only stop cells from cycling, at cytotoxic doses they kill rapidly dividing cells, and at toxic levels they kill all cells. The current application deals with inhibitory doses. There are roughly 210 epithelial cell types in the body, and only a small handful that are normally actively cycling. These include skin, hair, bone marrow, and gastrointestinal mucosa. Both skin and bone marrow cells cycle on a roughly 24 hour clock and as such would be similarly susceptible to cytotoxicity (i.e. nontoxic zone below 10 ng/ml for satratoxin and roridin and 200 ng/ml for T-2 and DAS). Since the blood would be the primary transdermal entry point for the trichothecenes a brief presentation of hematologic toxicity safety follows.

The average human contains ~5.5 liters of blood and 42 liters of extracellular water outside the vasculature (per HPIM p. 421 15Th Ed.). The blood circulates at roughly once every minute throughout the body in a resting state. Consequently, any trichothecenes that migrate into the blood would be almost instantly be mixed into 5.5 liters of blood.

The average human has ~18 square feet of skin (17,000 sq. cm.). At a normal epidermal thickness of 200 $\mu m$ this translates to 0.34 liters of epidermis. Psoriatic epidermis can be 5 to 10 times thicker (1 mm to 2 mm). Under a worst case scenario, if a human had 2 mm psoriatic plaque over 100% of their skin, they would have a total psoriatic epidermal mass of 3.4 liters.

Even though the Cleveland Infant Model clearly demonstrates the proclivity of macrocyclic trichothecenes to internalize into epithelium they come into contact with, without appreciably entering general circulation, a worst case scenario can be constructed to further demonstrate the safety of topical application of trichothecenes as presented in the example above. The worst case scenario requires that blood concentrations of macrocyclic trichothecenes never exceed 10 ng/ml for the two macrocyclic trichothecenes or 200 ng/ml for the two simple trichothecenes presented, to prevent any hematologic toxicity. The worst case scenario goes on to assume 0% of the trichothecene is absorbed by the epidermis or dermis, and 100% enters the blood stream Using the worst case scenario of 2 mm thick psoriatic epidermis over 100% of the skin and using the highest dose proposed under any scenario of present invention (i.e. $PIC_{100}$ of 1.0 ng/sq. cm for 2 mm thick epidermis) would mean 17,000 ng would be administered over the entire body. Continuing the worst case scenario that 0% of the trichothecene is absorbed by the skin and 100% passes directly into the blood—basically the 17,000 ng dose is injected directly into 5.5 liters of blood—the resulting blood concentration would be 3.09 ng/ml which is only 31% of the 10 ng/ml concentration determined not to reduce cell viability for the two macrocyclic trichothecenes and 1.5% of the concentration shown not to reduce cell viability for the two simple trichothecenes. Both are comfortably in the safety zone despite the unrealistically extreme assumptions used in constructing the worst case scenario. TABLE 4 summarizes the worst case scenarios using these extreme assumption for $PIC_{85}$ concentrations.

TABLE 4

Safety: $PIC_{85}$ Worst Case Scenarios
(2 mm thick psoriasis over 100% of body)
(0% of drug absorbed by skin; 100% enters blood)

| Trichothecene | $PIC_{85}$ Max. Dose | ng/ml blood | safe level | % of non toxic level |
|---|---|---|---|---|
| Roridin A | 8,500 ng | 1.55 ng/ml | 10 ng/ml | 16% |
| Satratoxin G | 10,800 ng | 1.98 ng/ml | 10 ng/ml | 20% |
| T-2 | 12,920 ng | 2.35 ng/ml | 200 ng/ml | 1% |
| DAS | 14,280 ng | 2.60 ng/ml | 200 ng/ml | 1% |

A further safety check can be performed by contrasting the unrealistically extreme 17,000 ng worst case dose of T-2 against AMRIID's computed LD50 (lethal dose to 50% of people) for T-2 by inhalation of 1.21 mg/kg of body weight. This translates to a 84,700,000 ng dose of T-2 being inhaled by a 70 kg person to have a 50% chance of survival. This contrasts with the 17,000 ng worst case topically applied dose (~5,000 times smaller) for T-2 possible under the dose determination section of this application. Magnuson et. al. cited a 2.0 mg/kg of body weight LD50 for topical application of T-2 in rats. Applying the rat model to humans would imply a 140,000,000 ng LD50 for topically applied T-2. Once again this is in stark contrast with the 17,000 ng (8, 235 times smaller) worst case topically applied dose for T-2 possible under the dose determination section of this application.

REFERENCES CITED

Referred to as "MBOC" in this application: Molecular Biology of the Cell, third edition, Garland Publishing, 1994, Bruce Alberts, Dennis Bray, Julian Lewis, Martin Raff, Keith Roberts, and James Watson.

Referred to as "HPIM" in this application: Harrison's Principles of Internal Medicine, 14th or 15th edition, McGraw Hill, 1998/2001, Fauci, Braunwald, Isselbacher, Wilson, Martin, Kasper, Hauser, Longo.

I claim:

1. A method of inhibiting the proliferation of psoriatic cells in humans or non-human animals, comprising topical application of a composition containing a therapeutically effective amount of a trichothecene or a mixture of trichothecenes directly onto a psoriatic area of skin on said humans or non-human animals.

2. The method of claim 1 wherein said trichothecene is a fragment or sub-unit of trichothecene which possesses the ability to inhibit protein synthesis.

3. The method of claim 1 or 2 wherein the trichothecene composition include a pharmaceutically acceptable carrier.

4. The method of claim 3 wherein the pharmaceutically acceptable carrier is selected from the group consisting of propylene glycol, ethanol, methanol, and dimethyl sulfoxide.

* * * * *